US006562581B2

(12) United States Patent
Law et al.

(10) Patent No.: US 6,562,581 B2
(45) Date of Patent: May 13, 2003

(54) METHOD FOR QUANTITATIVE DETERMINATION OF GLYCATED HEMOGLOBIN

(75) Inventors: Wai Tak Law, Moorestown, NJ (US); Yuri Nikolyukin, Moorestown, NJ (US)

(73) Assignee: Portascience, Moorestown, NJ (US)

( * ) Notice: Subject to any disclaimer, the term of this patent is extended or adjusted under 35 U.S.C. 154(b) by 0 days.

(21) Appl. No.: 09/943,674

(22) Filed: Aug. 31, 2001

(65) Prior Publication Data

US 2003/0073243 A1 Apr. 17, 2003

(51) Int. Cl.[7] .................................................. C12Q 1/54
(52) U.S. Cl. ............................................. 435/14; 436/67
(58) Field of Search .............................. 435/14; 436/67, 436/172, 175, 524; 549/213

(56) References Cited

U.S. PATENT DOCUMENTS

| 4,247,533 | A |   | 1/1981  | Cerami et al.    |         |
|-----------|---|---|---------|------------------|---------|
| 4,269,605 | A |   | 5/1981  | Dean et al.      |         |
| 4,270,921 | A |   | 6/1981  | Graas            |         |
| 4,351,711 | A |   | 9/1982  | Ambler           |         |
| 4,389,491 | A |   | 6/1983  | Hanamoto et al.  |         |
| 4,407,961 | A |   | 10/1983 | Sanders          |         |
| 4,436,820 | A |   | 3/1984  | Reiter           |         |
| 4,649,122 | A |   | 3/1987  | Lee              |         |
| 4,970,171 | A |   | 11/1990 | Messenger et al. |         |
| 5,206,144 | A |   | 4/1993  | Zeuthen et al.   |         |
| 5,431,793 | A | * | 7/1995  | Wang et al.      | 204/182.8 |
| 5,686,316 | A | * | 11/1997 | Fiechtner et al. | 436/518 |
| 5,877,025 | A | * | 3/1999  | Edwards et al.   | 436/67  |
| 5,882,935 | A | * | 3/1999  | Hirai et al.     | 436/67  |
| 5,919,708 | A |   | 7/1999  | Sundrehagen      |         |
| 6,162,645 | A | * | 12/2000 | Lee et al.       | 436/67  |
| 6,262,264 | B1| * | 7/2001  | Buck, Jr. et al. | 546/2   |

OTHER PUBLICATIONS

Frantzen F. Glycohemoglobin Filter Assay . . . Clinical Chemistry 43(12)2390–6, 1997.*
Blincko S. Non–Separation Assay for Glycohemoglobin. Clinical Chemistry 44(6)1302–8, 1998.*

* cited by examiner

*Primary Examiner*—Ralph Gitomer
(74) *Attorney, Agent, or Firm*—Iver P. Cooper

(57) ABSTRACT

A method and a system for separating glycated hemoglobin from non-glycated hemoglobin, and a method for one-read quantitative determination of the glycated hemoglobin and % $HbA_{1c}$ that does not require an additional measurement of total hemoglobin.

21 Claims, 3 Drawing Sheets

Phenylboronic acid
immobilized onto a
solid suport

HbA1c

Immobilized HbA1c

Blue dye

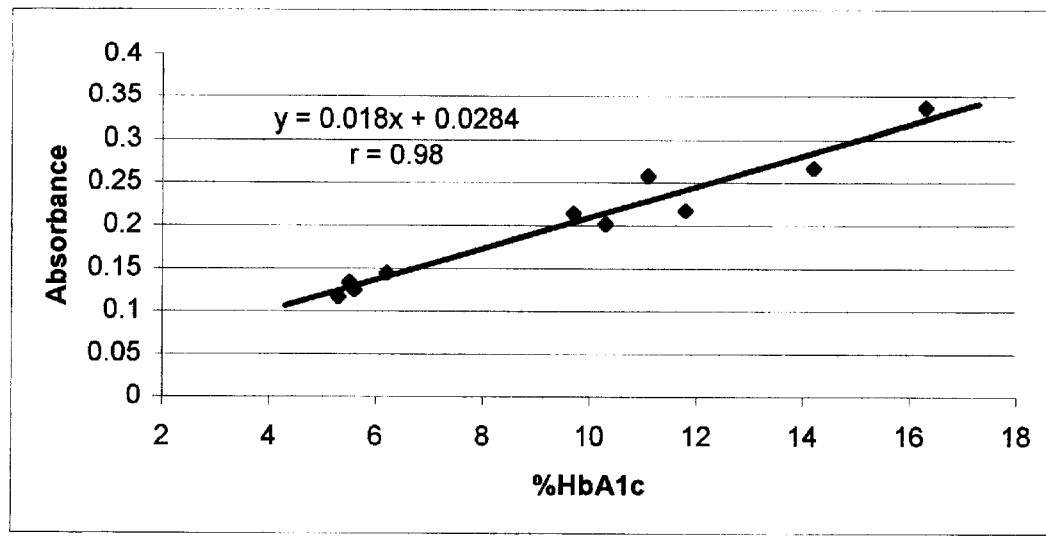
Fig.3
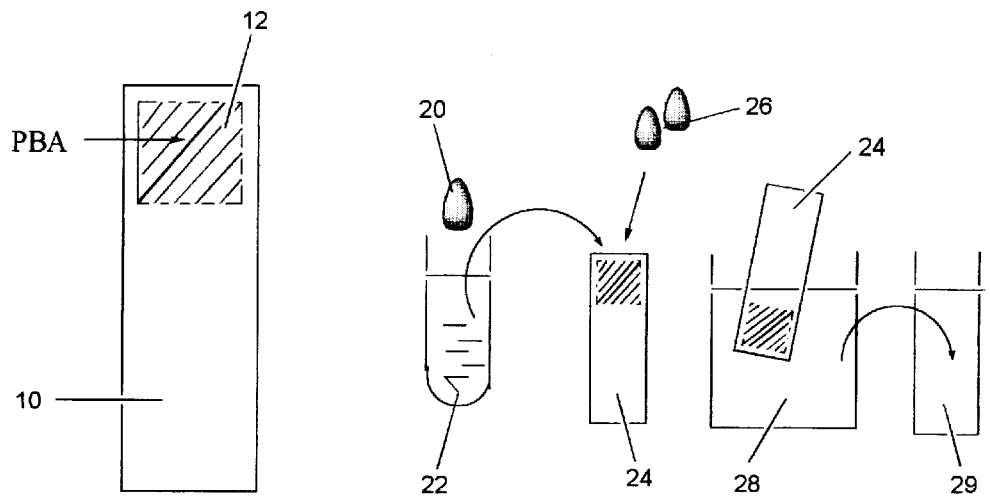
Fig. 4
Fig. 5

METHOD FOR QUANTITATIVE DETERMINATION OF GLYCATED HEMOGLOBIN

This invention was funded by a phase I SBIP grant from the National Institutes of Health, Grant No. 2R44DK58523.

FIELD OF THE INVENTION

The present invention relates to a novel method for measuring the concentration of glycated hemoglobin (gHb) and the percent hemoglobin $A_{1c}$ ($HbA_{1c}$) in blood without using antibodies, and more particularly, to a one-read method which does not require an additional measurement of total hemoglobin for assessing percentage hemoglobin $A_{1c}$

BACKGROUND OF THE INVENTION

The importance of diagnosis and monitoring of diabetes is emphasized by the American Diabetes Association reporting that 15.7 million Americans have diabetes, or 5.9% of the population. However, routinely used direct measurement of blood glucose level in patients has a limited value since it gives information only about the glucose concentration at the time of sampling and is influenced dramatically by diet. Nevertheless, an accurate index of a person's mean blood glucose level over 2 to 3 months can be provided by measurement of a specific type of glycated hemoglobin called the hemoglobin $A_{1c}$ concentration in blood [The Diabetes Control and Complications Trial Research Group, N. Engl. J. Med., 329, 977–986 (1993)]. Glycated hemoglobin, of which about 60% is represented by $HbA_{1c}$, is formed via nonenzymatic attachment of glucose to the hemoglobin molecule at a rate that is directly proportional to the ambient glucose concentration [Bunn H. F., Haney D. N., Gabbay K. H., Gallop P. N., Biochem. Biophys. Res. Commun., 67, 103–9 (1975) ].In the uncontrolled diabetic, the proportion of HbA,, may be increased three to four fold. For example, a healthy person may have an $HbA_{1c}$ concentration of 4.1–6.5% of the total hemoglobin, whereas in the diabetic the concentration may be up to 20%. Therefore, HbA,, measurement can provide diabetic patients an overview of their success in meeting long-term goals for controlling their blood glucose levels.

A variety of methods have been proposed for measuring HbA,, concentration in a sample of a patient's blood. They can be broadly divided into two categories on the basis of the principle used to separate glycated from unglycated hemoglobin components:

a) charge differences as in ion-exchange chromatography [U.S. Pat. No. 4,407,961, U.S. Pat. No. 4,649,122, U.S. Pat. No. 4,270,921, U.S. Pat. No. 4,389,491, U.S. Pat. No. 4,436,820] and in electrophoresis [U.S. Pat. No. 4,351,711]. Ion-exchange chromatography involves separation of hemoglobin fractions in microcolumns of ion exchange resin. Glycated hemoglobin elutes first while the non-glycated hemoglobin remains attached to the resin and can be removed by changing the eluting buffer. For proper separation, the composition, pH and ionic strength of the eluting buffer must be maintained within narrow limits. Additionally, the temperature control is critical. Subsequent spectrophotometrical measurement provides the amount of the fraction constituting the glycated hemoglobin. Electrophoresis exploits relative mobility of the hemoglobin fractions in a specially prepared agar medium in an electric field. Common drawbacks for these methods are poor reproducibility, sensitivity to variations in temperature, pH, ionic strength, and sample storage conditions. Also they require expensive equipment and usually prove too slow and cumbersome for practical use.

b) structural characteristics of the carbohydrate groups on the hemoglobin, as in immunoassay [U.S. Pat. No. 4,247,533, U.S. Pat. No. 4,970,171, U.S. Pat. No. 5,206,144] and boronate affinity chromatography [U.S. Pat. No. 4,269,605]. The major limitation of the immunoassay approach is the requirement of an additional independent measurement of the total hemoglobin in order to express the glycated hemoglobin level as a percentage number. Additionally, both immunoassay and high performance chromatography require very expensive reagents and equipment.

The approach based on the use of boronic acid derivatives as affinity matrices for $HbA_{1c}$ isolation is free from limitations that are characteristic for ion-exchange chromatography and electrophoresis and is the most widely accepted method. The representative example of the approach has been disclosed in International Publication No. WO 98/40750 and U.S. Pat. No. 6,162,645. Lee et al. proposed to measure percent of glycated hemoglobin using a single determination that includes incubation of a lysed whole blood sample (i.e. all the red blood cells in the sample has been ruptured) with magnetic microparticles that is coupled with boronic acid. The particles were then attracted to a magnet, washed, and a labeled antibody to human hemoglobin was added and the resulting signal was directly proportional to the %$HbA_{1c}$ in the sample. As it was mentioned above, the need of using antibody makes the method rather expensive.

Sundrehagen, in U.S. Pat. No. 5,919,708, proposed a four step assay for glycated hemoglobin which includes mixing a whole blood sample with a reagent containing agents that lyse erythrocytes, precipitate hemoglobin specifically and bind gHb by means of boronic acid conjugate with a blue dye. Then precipitated hemoglobin, conjugate-bound and unbound, is separated by filtration and washed to remove an excess of colored conjugate. The precipitate is evaluated by measuring the blue (gHb) and the red (total Hb) color intensity and the percentage of $A_{1c}$ is calculated. However this technique suffers from rather complex procedure which requires several manual operations.

Accordingly there is need to develop a simple, inexpensive non-antibody based method of detecting the amount of glycated hemoglobin in a blood sample using a single determination.

SUMMARY OF THE INVENTION

An object of the invention is to provide a method and a system for separating glycated hemoglobin from non-glycated hemoglobin, and a method for one-read quantitative determination of the glycated hemoglobin and %HbA,, that does not require an additional measurement of total hemoglobin.

The object of the invention can be achieved by exploiting of two characteristic features of glycated hemoglobin (gHb):
a) Structural Characteristic of the Carbohydrate Group.

The separation of glycated hemoglobin from a blood sample is based on the ability of boronic acids to form cyclic esters with 1,2-cis-diols presented in the glucose moiety of $HbA_{1c}$ molecule (FIG. 1). The isolation is carried out by diluting and lysing a blood sample with a buffer (pH 8–9) containing lysing agent and incubating the solution with boronic acid derivative (e.g., phenylboronic acid) immobilized onto a solid support. After incubation, the unbound hemoglobin is washed away with appropriate buffer.

b) Pseudo-peroxidative Properties of Hemoglobin.

Hemoglobin is known to exhibit pseudo-peroxidase activity (i.e. has catalytic ability like an enzyme such as peroxidase). Such activity can be measured by means of a material which undergoes a detectable change, generally a color change, in the presence of inorganic (e.g., hydrogen peroxide) or organic peroxides. There are many compositions which can be used for this determination, including mono- and diamines, phenols, polyphenols, leucodyes, and other compounds or two component systems which produce colors under the conditions of the assay. of the assay. (FIG. 2).

BRIEF DESCRIPTION OF THE DRAWINGS

FIG. 3 is a graphical representation of the correlation of optical absorbance with per cent $HbA_{1c}$ for Example 1.

FIG. 4 is a schematic drawing of a dip stick format for the present invention.

FIG. 5 is a schematic representation of the dip stick procedure of Examples 2 and 3.

DETAILED DESCRIPTION OF THE INVENTION

Figure 1:
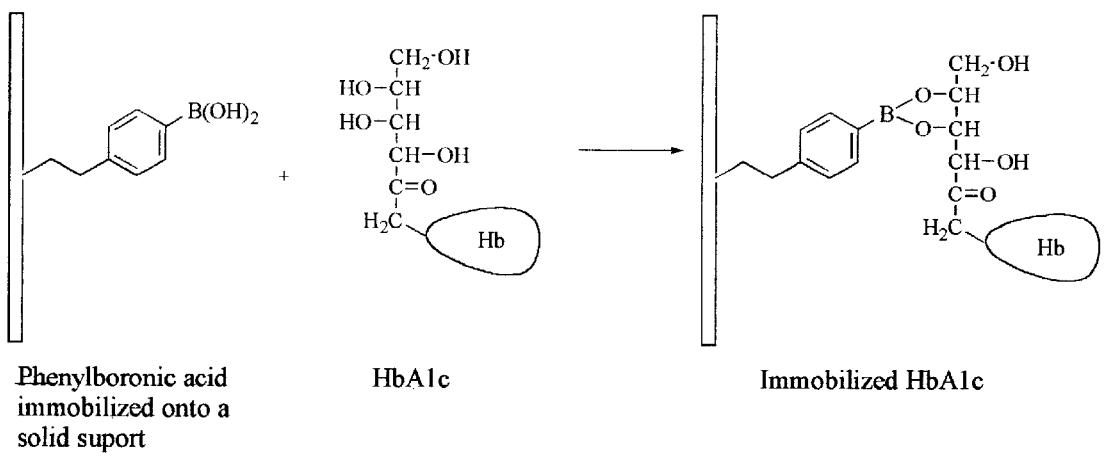
FIG. 1 is a schematic representation of the immobilization of the $HbA_{1c}$ molecule on a solid support material.
Figure 2:
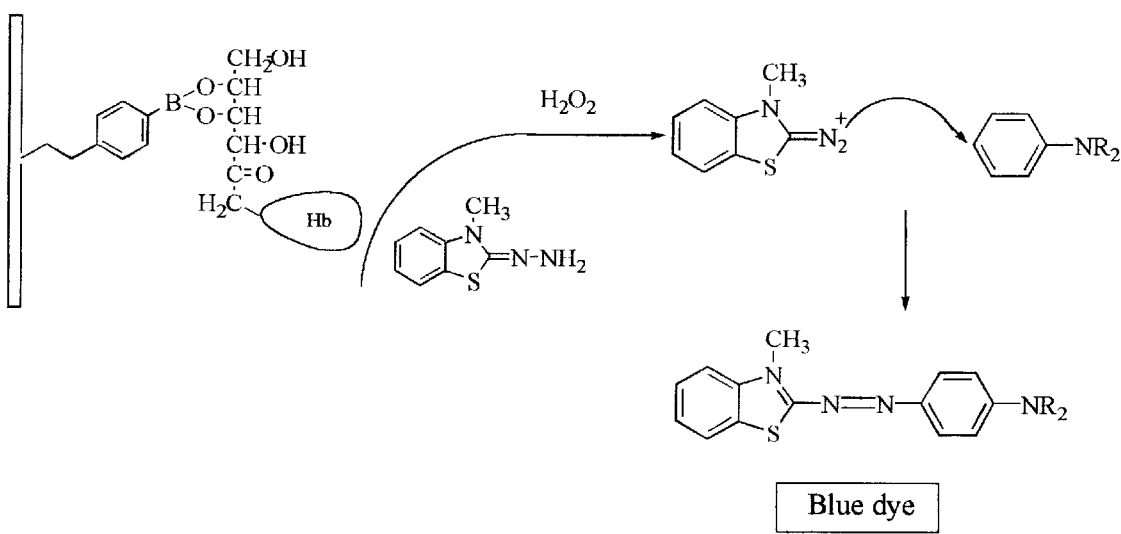
FIG. 2 is a schematic representation of dye formation for an immobilized $HbA_{1c}$ molecule.

More particularly, the present invention is directed to a method for a one-read determination of the percentage of $HbA_{1c}$ in the total hemoglobin of a blood sample. The method involves the incubation of the diluted and lysed blood sample with a boronic acid derivative immobilized onto a solid support, separation of the gHb-boronic acid conjugate, quantitative determination of the bound gHb using its peroxidase-like properties with an appropriate substrate, and the report of a standardized $\%HbA_{1c}$ value using a single measurement.

The blood sample may be diluted and lysed with deionized water. To shorten the assay process, however, an accelerating lysing agent is preferably included. Typically, nonionic surfactants such as Triton X-100 (Union Carbide Corp.) or sapogenin (e.g., Saponin S7900, Sigma-Aldrich Corp.) can be used for this purpose.

The preferred boronic acid derivatives are arylboronic acids having a functional group that can be used for immobilization onto a solid support, e.g., hydroxy, primary and secondary amino, aldehyde, carboxylic, and the like, selected so as to react with groups available on the substrate surface to form covalent bonds e.g., carboxylic groups reacting with primary amino groups. For the purposes of this invention, m-aminophenylboronic acid is an exemplary and preferred boronic acid compound. Immobilization of the boronic acid derivative onto a solid support is conventional and fully understood by those in the art [G. T. Hermanson et al. "Immobilized Affinity Ligand Techniques", Academic Press: London, 1992]. Suitable materials to which the boronic acid derivative can be covalently conjugated include either inorganic (e.g., silica gel) or organic (e.g., polymeric materials) matrices. The polymeric material can comprise natural or synthetic materials and may take the form of beads or a sheet of fabric (e.g., woven fabric) or any other shape. Another example of a solid support is magnetic particles coated with a polymer bearing suitable functional groups.

The separation of gHb from a blood sample is carried out by mixing the immobilized boronic acid derivative with the blood sample diluted with an appropriate buffer solution. The formation of the cyclic ester between dihydroxyboryl group of the boronic acid derivative and the 1,2-cis-diol group presented in the carbohydrate moiety of $HbA_{1c}$ molecule proceeds the most efficiently at high pH values. The preferred pH range of the reaction is 7.5–10.0. A number of buffer solutions can be used, among them phosphate, glycine, ammonium acetate, CAPS, taurine, and others capable of maintaining a suitable pH of the reaction mixture.

After the separation, the amount of bound gHb can be determined by taking advantage of its pseudo-peroxidase properties. The boronic acid-$HbA_{1c}$ conjugate when mixed with an appropriate dye developing solution that is catalyzed by a peroxidase to form a dye provides a unique advantage for the present invention: other blood glycated proteins that bind to the solid support, e.g., glycated albumin, will not have to be separated out using antibody or other means since they do not process the Another important advantage of the present approach is that the nature of the hemoglobin enzymatic activity can be used to enhance the method sensitivity. The hemoglobin acts as a catalyst, providing amplification of the signal by generating many copies of the colored dye without being consumed in the reaction.

Compositions that can be used for color development for this determination include but not limited to mono- and diamines, phenols, polyphenols, leucodyes, and other compounds or color forming systems which produce color under conditions of the assay. Examples of leucodyes include triarylmethanes, xanthenes, styryl dyes, and azine dyes such as phenazines, phenoxazines, and phenothiazines in their reduced colorless form. A color forming system usually consists of a color forming coupler (e.g., N-substituted anilines) and an oxidizable color-developing compound (e.g., 4-aminoantipyrine or 3-methylbenzothiazolone-2 hydrazone).

According to the present invention, the separated gHb-boronic acid conjugate is mixed with the developing solution which comprises an appropriate buffer, one of the mentioned above color forming compounds or systems, and a peroxide. The mixture is allowed to stand at room temperature for a fixed amount of time. During this period of time the following reaction occurs:

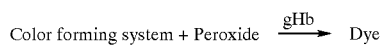

$$\text{Color forming system} + \text{Peroxide} \xrightarrow{\text{gHb}} \text{Dye}$$

Immobilized hemoglobin catalyzes the oxidation of the color forming system to form a dye. The dye concentration in the sample is directly proportional to the amount of bound glycated hemoglobin and can be measured using a spectrophotometer.

Surprisingly, it was found that the amount of glycated hemoglobin captured by immobilized boronic acid is in direct proportion to the %gHb in the sample. This permits the accurate determination of the percent glycated hemoglobin in a single measurement. The measured percent glycated hemoglobin value can be reported in a standardized $HbA_{1c}$ value. The standardization of $HbA_1$ is based on recommendations from NGSP (National Glycohemoglobin Standardization Program).

The present invention can be configured in a variety of forms in either liquid or solid phase formats. Assay devices can be constructed in elements known in the art as test strips, diagnostic elements, dip sticks, diagnostic agents and the like. Useful elements can be prepared from paper, porous particulate structures, cellulose, wood, glass fibers, woven and non-woven fabrics (both synthetic and natural) and the like. The components of the analytical composition, as well as any peroxidative substances, immobilized boronic acid derivatives, interactive components, etc., can be incorporated into a multilayer or a capture or a filtration device. The location of individual components is well within the skill of a person in the chemical arts.

Assays for the present invention can be manual or automated. The following examples are given for purpose of illustration only, and are not meant to be limiting of the scope of the invention.

EXAMPLE 1

Manual Format

Whole blood sample (100 µl) was mixed with 250 µl of binding buffer (Taurine, pH9) and the mixture was incubated with 25 mg of 3-aminophenylboronic acid immobilized onto acrylic beads (Sigma, Cat.# A 4046, Ligand immobilized: 300–600 µmoles per gram)) for 10 minutes. The beads were filtered off and washed with phosphate buffer (50 mM, pH7). The beads were transferred into a vial, and color development solutions containing the color forming coupler and the oxidizable color-developing compound were added in the following order:

phosphate buffer (50 mM, pH7) . . . 2.7 ml
3-methyl-2-benzothiazolinone hydrazone hydrochloride solution (MBTH)(0.035%) . . . 100 µl
N,N-diethylaniline (0.08M) . . . 100 µl Finally 100 µl of $H_2O_2$ (20 mM) was added. The mixture was gently agitated at room temperature for 3 minutes, and the absorbance readings at 596 nm were measured on a spectrophotometer. Ten blood samples with $HbA_{1c}$ values in the range 5.3–16.3% were tested. All the samples were also tested with the reference HPLC (High Pressure Liquid chromatography) method. The results are shown in Table 1.

TABLE 1

| Sample No. | % $HbA_{1c}$ by HPLC | Absorbance |
|---|---|---|
| 1 | 5.3 | 0.117 |
| 2 | 5.5 | 0.134 |
| 3 | 5.6 | 0.125 |
| 4 | 6.2 | 0.145 |
| 5 | 9.7 | 0.214 |
| 6 | 10.3 | 0.201 |
| 7 | 11.1 | 0.258 |
| 8 | 118 | 0.217 |
| 9 | 14.2 | 0.267 |
| 10 | 16.3 | 0.336 |

When the absorbance values obtained by the proposed method were plotted versus the reference HPLC method, a respectable correlation coefficient of r=0.98 was obtained (FIG. 3), indicating that the current invention yields %$HbA_{1c}$ data that correlates well versus the reference HPLC method.

EXAMPLE 2

Dip Stick Format (Spectrophotometric Measurement)

The key component of the proposed device is a membrane attached to a plastic strip (FIG. 4) The membrane 12 contains immobilized phenylboronic acid (PBA) and is attached to a backing 10 Biodyne® C membrane(Pall Gelman Lab., Ann Arbor, Mich.) used in this example is a nylon 6,6 membrane with pore surface populated by carboxylic groups. Onto this membrane is immobilized 3-Aminophenylboronic acid (APBA) using dicyclohexylcarbodiimide (DCC) to form covalent amide bonds.

Immobilization was accomplished by incubating of the membrane with a solution of APBA and DCC in tetrahydrofuran (THF) for two days at ambient temperature. An excess of APBA was used to block all carboxylic groups and prevent nonspecific binding. In order to remove reaction components, the membrane was washed successively with dimethylformamid (DMF), THF and acetone. The washing continued until the washing solution showed no absorbance in the 200–300 nm region. The membrane was then dried and stored in a dessicator. A piece of the dried membrane (5×5 mm) was attached to a plastic strip by means of double-side tape.

The reagents used in the assay were as follows:

Binding buffer—0.1 M Taurine buffer adjusted to pH=9 with sodium hydroxide solution:
Saponin/binding buffer solution (2.5 mg/10 ml)
Phosphate buffer (50 mM, pH=7)
MBTH HCl solution (35 mg/100 ml of water)
N-ethyl-N-(3-aminopropyl)aniline dihydrochloride (NEAP 2HCI) solution (0.2 g/10 ml of water) $H_2O_2$ solution (1 ml 3% $H_2O_2$/9 ml of water) 9 ml

The Assay Procedure

The testing protocol is illustrated in FIG. 5 and includes the following steps:

1. Diluting and lysing the blood sample 20 with binding buffer 22.
2. Introducing the mixture from Step 1 to the membrane 24.
3. Washing the membrane 24 with a wash solution 26.
4. Treating the membrane 24 with a developing solution by dipping the strip into a fixed volume of substrate solution 28 for a fixed period of time,
5. transferring the supernatant substrate solution to a quartz cuvette 29; and
6. measuring the %$HbA_1$ using a spectrophotometer. More specifically, The blood sample (10 ul) was lysed by mixing with the saponin/binding buffer solution (790 ul). The strip with the attached membrane was immersed into the mixture and incubated for 5 minutes. The strip was washed with tap water for 1 minute and incubated for 5 minutes with the following developing solution:

phosphate buffer—360 µl;
MBTH solution—30 µl;
NEAP solution—30 µl;
$H_2O_2$ solution—30 µl.

The colored dye created at the end of the assay forms in a liquid phase—supernatant—that is in contact with the membrane. The supernatant was drawn off and the color intensity was determined by reading the absorbance in a spectrophotometer. The resulting data are shown in Table 2.

TABLE 2

| Sample No. | % HbA$_{1c}$ by HPLC | Absorbance |
| --- | --- | --- |
| 1 | 5.1 | 0.142 |
| 2 | 5.1 | 0.100 |
| 3 | 5.4 | 0.140 |
| 4 | 5.4 | 0.100 |
| 5 | 5.4 | 0.120 |
| 6 | 5.7 | 0.150 |
| 7 | 5.7 | 0.130 |
| 8 | 5.8 | 0.120 |
| 9 | 6.7 | 0.290 |
| 10 | 6.9 | 0.145 |
| 11 | 7.2 | 0.230 |
| 12 | 8.3 | 0.170 |
| 13 | 8.3 | 0.170 |
| 14 | 9.0 | 0.316 |
| 15 | 9.8 | 0.426 |
| 16 | 9.8 | 0.330 |
| 17 | 10.3 | 0.290 |
| 18 | 11.1 | 0.340 |
| 19 | 11.5 | 0.530 |
| 20 | 14.7 | 0.730 |
| 21 | 16.7 | 0.800 |

When the absorbance values obtained by the proposed method were plotted versus the reference HPLC method, a respectable correlation coefficient of r=0.95 was obtained, indicating that the current invention gives % HbA$_{1c}$ data that correlates well versus the reference HPLC method.

Example 3

Dip Stick Format (Reflectometric Measurement)

In order to fix dye formed during the test to the membrane surface, NEAP was immobilized onto the membrane along with APBA. A piece of Biodyne C Membrane (4×4 cm) was incubated with a solution of APBA (80 mg) and DCC (0.2 g) in dry THF (8 ml) for 24 hours. The membrane was washed by agitating with following solvents for 15 min each: THF (4×5 ml), DMF (15 ml), THF (15 ml), and acetone (2×15 ml). The washed membrane was briefly dried under the hood and incubated for 24 hours with a solution of NEAP 2HCl (0.25 g), diisopropylethylamine (0.4 ml) and DCC (0.8 g) in dry DMF (10 ml). The membrane was washed by agitating with following solvents for 15 min each: THF (2×15 ml), DMF (15 ml), THF (15 ml), and acetone (2×15 ml). A dip stick was produced from the dried membrane as in Example 2.

The assay procedure was generally the same as in Example 2 except that the colored dye is trapped/fixed on the membrane. A Chroma Meter (Minolta, Remsey, N.J.) was used to measure the color intensity of the reflected light from the developed membrane. Results are shown in Table 3.

TABLE 3

| % HbA$_{1c}$ | Minolta readings | Mean |
| --- | --- | --- |
| 5.0 | 18.50; 17.82 | 18.1 |
| 5.5 | 20.05; 19.76 | 20.0 |
| 12.4 | 23.34; 23.58 | 23.5 |
| 14.5 | 23.78; 23.78 | 23.8 |
| 16.7 | 28.71; 28.21 | 28.4 |

Example 4

ICON Format

Figure 6:
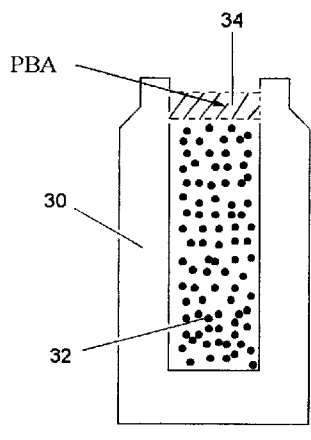
FIG. 6 is a schematic drawing of an immunoconcentration (ICON) device of the type used in Example 4.
Figure 7:
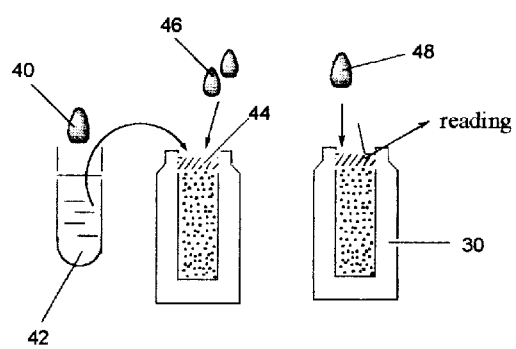
FIG. 7 is a schematic representation of the ICON format for the present invention.

The assay can also be constructed in an ICON (Immunoconcentration Device) format. This is a popular disposable rapid test format that includes a substrate membrane, flow control filter, an absorbent matrix, and the device housing. As is shown in FIG. 6, the membrane coated with PBA is placed inside a plastic casing 30 on top of some liquid absorbance material 32. After the blood sample 40 (FIG. 7) is mixed the binding buffer 42, it is introduced onto the membrane 44, followed by a wash solution 46, then a developing solution 48 containing the dye precursors and peroxide. The absorbance material pulls all excess wash and substrate solution away form the membrane surface, and the fixed time color density was read by a handheld reflectometer.

Example 5

Disposable Flow Cassette Format

Figure 8:
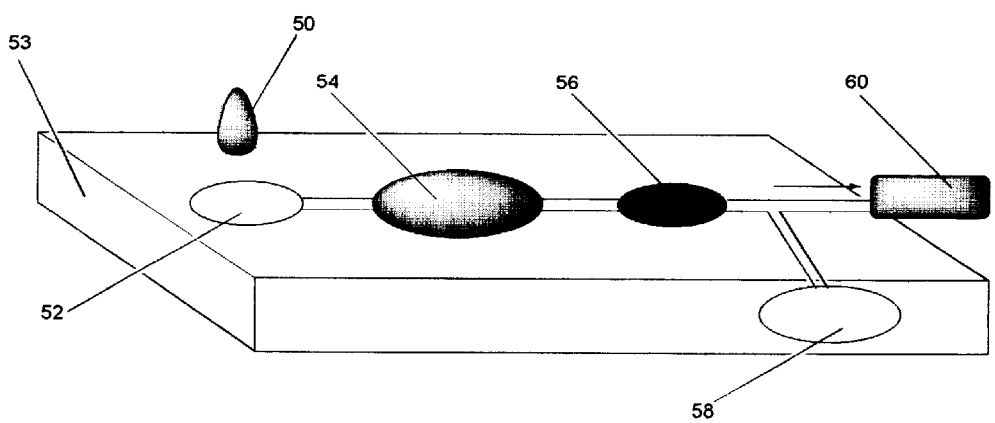
FIG. 8 is a schematic representation of the disposable flow cassette format for the present invention.

The assay can also be performed in a flow-through cell format with the aid of a pump (FIG. 8). Detailed description of such cuvettes can be found, inter alia, in U.S. Pat. No. 5,731,212 to Gavin, et al. The pump automates all the fluid handling steps and allows the assay be performed in essentially one step. Whole blood sample 50 will be deposited into a sample well 52 on a disposable cassette 53. The pump will measure a predetermined volume of the whole blood sample and dilute it with a lysing agent and a buffer. The mixture is transported into the capture zone 54 using a pump 60. Phenylboronic acid either immobilized on particles, membrane or directly on the surface of the capture zone 54 captures the gHb. After a period of incubating time, the mixture is transported downstream, while a wash solution, followed with a developing solution, will be passed through the capture zone 54. The captured gHb molecules will remain in the capture zone 54, while the other form of Hb will be washed and carried to the waste 58. The developing solution contains a peroxide and a dye solution, and the gHb catalyzes color development. The colored solution will be transported to the reading zone 56 and read either by reflectance, fluorescent, transmittance, or other spectrophotometric means, and the signal will be proportional to the % HbA$_{1c}$ in the sample.

What is claimed is:

1. A method for quantitative determination of HbA$_{1c}$ without using antibodies comprising:
   a. incubating a diluted and lysed blood sample comprising a glycated hemoglobin (gHb) with a boronic acid derivative immobilized on a solid support to form a gHb-boronic acid conjugate;
   b. separating the gHb-boronic conjugate from the sample;
   c. adding a dye developing solution that is catalyzed by a peroxidase to form a dye and incubating the gHb-boronic conjugate with the dye developing solution to form a dye; and
   d. measuring the dye concentration, which is directly proportional to the amount of bound glycated hemoglobin.

2. The method according to claim 1 wherein the boronic acid derivative is selected from the group consisting of arylboronic acids having a functional group which can be immobilized onto a solid support.

3. The method according to claim 2 wherein the functional group is selected from the group consisting of hydroxy, primary amino, secondary amino, aldehyde, and carboxylic groups.

4. The method according to claim 3 wherein the boronic acid derivative is m-aminophenylboronic acid.

5. The method according to claim 1 wherein the solid support is selected from the group consisting of beads, fabric sheets, polymer sheets, membranes, and magnetic particles coated with a polymer.

6. The method according to claim 1 wherein the incubation is conducted at a pH of from 7.5 to 10.0.

7. The method according to claim 1 wherein the dye developing solution contains a dye developing compound selected from the group consisting of monoamines, diamines, phenols, polyphenols, and leucodyes.

8. The method according to claim 7 wherein the dye developing compound is selected from the group consisting of triaryl methanes, xanthenes, styryl dyes, and azine dyes.

9. The method according to claim 1 wherein the dye developing solution comprises a color forming coupler and an oxidizable color-developing compound.

10. The method according to claim 9 wherein the color forming coupler is selected from the group consisting of N-substituted anilines.

11. The method according to claim 10 wherein the dye-developing compound is selected from the group consisting of 4-aminoantipyrine and 3-methylbenzothiazolone-2-hydrazone.

12. The method according to claim 1 wherein the boronic acid derivative is immobilized on a solid support selected from the group consisting of paper, porous particulates, cellulose, wood, glass fibers, membranes, woven fabrics, and nonwoven fabrics.

13. The method according to claim 1 wherein the peroxidase activity is obtained from the hemoglobin pseudoperoxidase activity.

14. In a method for quantitative determination of $HbA_{1c}$ without using antibodies, the improvement comprising formation of a detectable gHb-boronic acid conjugate.

15. The method according to claim 14 wherein the detectable gHb-boronic acid conjugate is detected by a dye developing solution that is catalyzed by a peroxidase to form a dye.

16. The method according to claim 15 wherein the dye developing solution comprises a color forming coupler and an oxidizable color-developing compound.

17. The method according to claim 16
wherein the dye developing solution contains a dye developing compound selected from the group consisting of monoamines, diamines, phenols, polyphenols, and leucodyes.

18. The method according to claim 17 wherein the dye developing compound is selected from the group consisting of triaryl methanes, xanthenes, styryl dyes, and azine dyes.

19. The method according to claim 14 wherein the gHb-boronic acid conjugate is formed with a boronic acid derivative having a functional group which can be immobilized onto a solid support.

20. The method according to claim 17 wherein the boronic acid derivative is immobilized on a solid support.

21. The method according to claim 20 wherein the solid support is selected from the group consisting of beads, nonwoven fabric sheets, woven fabric sheets, polymer sheets, membrane, magnetic particles coated with a polymer, paper, porous particulates, cellulose, wood, and glass fibers.

* * * * *